(12) United States Patent
Jensen et al.

(10) Patent No.: US 10,863,941 B2
(45) Date of Patent: Dec. 15, 2020

(54) DEVICE FOR REGULATING A VOLUMETRIC FLOW

(71) Applicant: MEDICAL MEASUREMENT SYSTEMS B.V., Enschede (NL)

(72) Inventors: Michael Gondy Jensen, Jyderup (DK); Kristine Larsen, Munich (DE); David Van Gorkom, Prien am Chiemsee (DE); Jens Witte, Munich (DE)

(73) Assignee: MEDICAL MEASUREMENT SYSTEMS B.V., Enschede (NL)

(*) Notice: Subject to any disclaimer, the term of this patent is extended or adjusted under 35 U.S.C. 154(b) by 651 days.

(21) Appl. No.: 14/772,355

(22) PCT Filed: Feb. 28, 2014

(86) PCT No.: PCT/EP2014/053970
§ 371 (c)(1),
(2) Date: Sep. 2, 2015

(87) PCT Pub. No.: WO2014/135458
PCT Pub. Date: Sep. 12, 2014

(65) Prior Publication Data
US 2016/0007901 A1  Jan. 14, 2016

(30) Foreign Application Priority Data
Mar. 4, 2013 (DE) .................. 10 2013 102 084

(51) Int. Cl.
*A61B 5/20* (2006.01)
*A61M 39/28* (2006.01)
*A61M 5/168* (2006.01)
*A61B 5/03* (2006.01)
*A61B 5/00* (2006.01)

(52) U.S. Cl.
CPC .............. *A61B 5/205* (2013.01); *A61B 5/036* (2013.01); *A61M 5/16813* (2013.01); *A61M 5/16881* (2013.01); *A61M 39/28* (2013.01); *A61B 5/6852* (2013.01); *A61M 2205/3331* (2013.01)

(58) Field of Classification Search
CPC ... A61B 5/205; A61B 5/0215; A61B 5/14532; A61B 5/412; A61B 5/036; A61B 5/6852; A61M 1/3639; A61M 39/286
See application file for complete search history.

(56) References Cited

U.S. PATENT DOCUMENTS 3,779,507 A * 12/1973 Clarke ................ A61M 39/284
251/4
3,877,428 A * 4/1975 Seagle ............. A61M 5/16877
604/248

(Continued)

FOREIGN PATENT DOCUMENTS

DE            02026127 B2       12/1971

*Primary Examiner* — Patrick Fernandes
(74) *Attorney, Agent, or Firm* — Douglas Denninger (57) ABSTRACT

A hose segment, and a device for using the hose segment, to regulate a volumetric flow rate, including the hose segment through which fluid can flow, and a hose clamp including a basic housing having an accommodating region for the hose segment and a clamping element that can be moved between at least two regulation positions. The clamping element has an effect on the hose segment in interaction with segments of the accommodating region as pressing points at least in one regulation position.

19 Claims, 5 Drawing Sheets

(56) References Cited

U.S. PATENT DOCUMENTS

| | | | |
|---|---|---|---|
| 4,551,134 A * | 11/1985 | Slavik | A61M 5/16809 128/DIG. 13 |
| 4,621,647 A | 11/1986 | Loveland | |
| 5,827,243 A | 10/1998 | Palestrant | |
| 6,056,697 A | 5/2000 | Owens et al. | |
| 6,725,726 B1 | 4/2004 | Adolfs et al. | |
| 2003/0200812 A1 | 10/2003 | Kuhn et al. | |
| 2004/0006321 A1 | 1/2004 | Cheng et al. | |
| 2004/0050168 A1 | 3/2004 | Uberreiter | |
| 2005/0065408 A1 | 3/2005 | Benderev | |
| 2007/0038143 A1 | 2/2007 | Christensen et al. | |
| 2008/0250340 A1 | 10/2008 | Dlugos et al. | |
| 2009/0131768 A1 | 5/2009 | Simpson et al. | |
| 2009/0221933 A1 | 9/2009 | Nishtala et al. | |
| 2009/0312719 A1 * | 12/2009 | Chew | A61M 39/286 604/251 |
| 2014/0100526 A1 | 4/2014 | Ueda et al. | |

\* cited by examiner

DEVICE FOR REGULATING A VOLUMETRIC FLOW

CROSS-REFERENCE TO RELATED APPLICATIONS

This application is a national phase filing under 35 USC § 371 of international application No. PCT/EP2014/053970 filed 28 Feb. 2014, which claims priority to German Application No. 10 2013 102 084.4 filed 4 Mar. 2013. This application also cross-references the following two international applications by the same inventors and having the same filing dates in the US, WIPO and Germany: PCT/EP2014/053968 for "Pressure-Measuring System" and PCT/EP2014/053967 for "Device For Measuring Pressure In A Fluid". The entire contents of each of the above-mentioned applications are incorporated herein by reference.

FIELD OF THE INVENTION

The present invention relates to a device for regulating a volumetric flow, more particularly for use in medical diagnosis, especially in urodynamics and gastroenterology, and a hose segment for use in a corresponding device for regulating a volumetric flow.

BACKGROUND OF THE INVENTION

In the prior art, diagnostic pressure measurement is particularly known in urodynamics. During the pressure measurement with water-filled catheters, the pressure in the body is diverted via a water column, which passes through the lumen of the catheter and the pressure transmission hoses, to external pressure sensors. There the pressure in the body is then measured, including a hydrostatic pressure which results from the difference in height between the measurement indicator and measuring location. This pressure offset is compensated either through defined positioning of the sensors (at the pubic bone in urodynamics) or through electronic zeroing.

Figure 1:
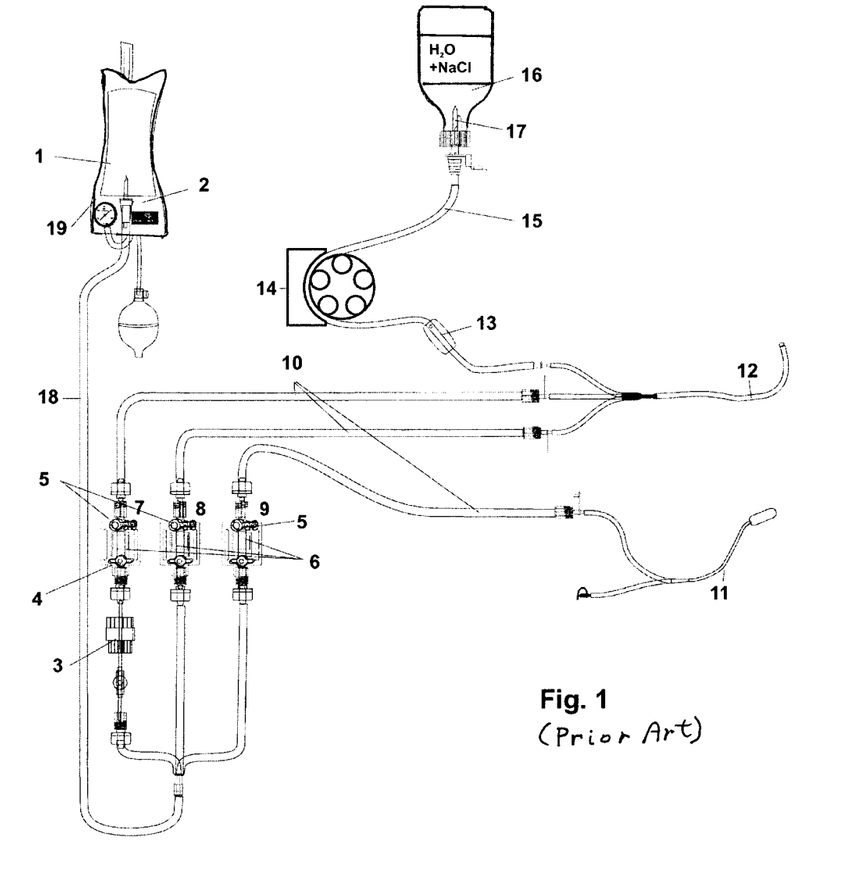
FIG. 1 shows the structure of a measuring system in accordance with the prior art.

Today, a urodynamic examination requires a considerable amount of preparation and a large number of sterile disposable articles are required. A pump hose, a perfusion hose, three measurement indicators each with a three-way and a two-way valve, three pressure transmission hoses, a transurethral catheter with a filling volume and two measuring volumes and a rectal catheter with a balloon, which all have to be assembled and prepared on site (FIG. 1).

Disadvantageous here in particular is also that a plurality of valves has to be provided which have to be set to different positions for preparing the examination and also have to be operated for the examination in accordance with a predetermined sequence plan.

SUMMARY OF THE INVENTION

On this basis of this prior art it is now the aim of the present invention to provide a device for regulating a volumetric flow with which the known drawbacks in the prior art are at least partially overcome/improved.

This is achieved through a device in accordance with the invention for regulating a volumetric flow according to claim 1 and a hose segment for use in this device for regulating a volumetric flow according to claim 13. Preferred forms of embodiment of the device and the hose segment are the subject matter of the relevant sub-claims. The invention also covers the use of the invented device for regulating a volumetric flow and the corresponding hose segment in the field of urodynamics and gastroenterology, more particularly for bladder, rectal and urethral pressure measurement.

The invented device for regulating a volumetric flow comprises at least one hose segment through which fluid can flow and a hose clamp, wherein the hose clamp comprises a basic housing with an accommodating region for the hose segment and a clamping element that can be moved between two, preferably between three, regulation positions. The clamping element acts on the hose segment and its lumen with at least one section of the accommodating region as a pressing point in at least one regulation position, wherein in the region of at least one regulation position a spacer is arranged in the lumen of the hose segment.

In accordance with the present invention at least the device for regulating the volumetric flow can be set to two or three regulation positions, covering the positions "open", "closed" and/or "perfused". In the "open" position the lumen of the hose segment is completely passable, whereas in the "closed" position the lumen of the hose segment is completely closed. In the perfused position, through the spacer, which is preferably arranged in the inside of the lumen, the lumen is partially, more particularly slightly open.

In accordance with the present invention perfused, i.e. slightly open, is taken to mean a setting in which under predetermined conditions the volumetric flow, determinable by way of the device for regulating the fluid flow, is restricted to between 0.1 ml/min and 8 ml/min, preferably between 0.5 ml/min and 5 ml/min.

Such a setting is necessary, if very small volumetric flows are necessary in order to be able to undertake corresponding pressure measurements in a dynamic system. In accordance with the present invention such volumetric flows are considered as slight, as in comparison with the normal/maximum volumetric flow they are relatively small.

In accordance with the present invention the spacer is an integral component of the hose segment and/or is formed by an elongated, more particularly a thread-like or rod-like element, which at least in sections is connected positively, non-positively or bonded to the hose segment. More particularly, the spacer serves to reduce the lumen to a value of between 0.01% to 5%, preferably between 0.1% and 1%, and more particularly around 0.5% so that through this the lumen of the hose segment in the perfused setting is slightly open and a volumetric flow of between 0.1 ml/mm and 8 ml/mm, preferably between 0.5 ml/min and 5 ml/min is provided.

The spacer is also at least partially made of a material selected from a group that preferably includes plastic, wool, cotton, cellulose, metal, combinations thereof and suchlike and, in particular, has a cross-sectional shape which is quadratic, rectangular, oval, circular, square or suchlike. In addition, the spacer is arranged in the lumen of the hose segment in such a way that the lumen is irregularly reduced.

In accordance with a further, particularly preferred form of embodiment of the present invention the hose segment is made of a flexible material, more particularly a flexible plastic, and is squeezable in sections, wherein additionally and preferably it has a small inner diameter which is preferably between 0.2 mm and 10 mm, preferably between 0.5 mm and 5 mm and more particularly around approx. 3 mm.

In accordance with a further particularly preferred form of embodiment of the present invention the lumen of the hose segment is irregularly reduced by the spacer, i.e. on squeezing the lumen cannot be completed closed by the inner walls of the hose, but there remains at least in the immediate region of the spacer a lumen area through which the fluid can flow.

Considered as fluids in accordance with the present invention are flowable systems, more particularly liquids, which are, for example, used in medicine and medical technology. Examples of these can be infusion solutions such as sodium chloride solution, water, aqueous solutions, solutions for injection, solutions for infusion, nutritional solutions, electrolyte solutions, blood, plasma, gas, air, combinations thereof and suchlike.

In accordance with a further particularly preferred form of embodiment these fluids are stored in fluid reservoirs which, in turn, are also known in the prior art, in the form of infusion bottles or infusion bags for example.

In accordance with a particularly preferred form of embodiment of the present invention the device for regulating a volumetric flow is characterised in that the regulation positions are brought about by at least one hose clamp, wherein the clamping element is arranged in a rotating manner extending radially around the centre of rotation. In particular the section of the clamping element closest to the centre of rotation interacts with at least one pressing point of the housing accommodation of housing accommodation region as a counter-pressure element.

In an alternative, but also particularly preferred form of embodiment the clamping element is moved by means of a motor, more particularly a multiphase motor or a servo motor, between the regulation positions and preferably held/stopped in these accordingly. For the individual positions stopping mechanisms can be provided or the multiphase motor or servo motor provides stops at the relevant positions. Alternatively the clamping element can also be moved into the appropriate position and, if necessary, mechanically fixed manually.

In a further particularly preferred form of embodiment of the present invention, the device for regulating a volumetric flow, the hose clamp/hose clamp segment or at least parts thereof are made of a material that is selected from a group that includes duroplastic or thermoplastic synthetic materials, and more particularly polyphenylene sulphide, polypropylene, poly-1-butene, polyvinyl chloride, polyvinylidene chloride, polymethyl methacrylate, polyacryl nitrile, polystyrene, polyacetal, polyvinyl alcohol, polyvinyl acetate, ionomers, fluoroplastic, polyethylene, polyamide, more particularly partially aromatic polyamide, polycarbonate, polyester, polyphenylene oxide, polysulphone, polyvinyl acetal, polyurethane and chlorinated polyether, cellulose nitrate, cellulose acetate, cellulose ether, phenol resin, urea resin, thiourea resin, melamine resin, alkyl resin, allyl resin, silicone, polyimide, polybenzimidazole, epoxy resin, casein plastic, cross-linked polyurethane, unsaturated polyester resin, acrylnitrile butadiene styrene, acrylester styrene acrylonitrile, metals such a stainless steel, aluminium, combinations thereof and suchlike.

In addition to the device for regulating a volumetric flow, the present invention also comprises at least one hose segment of a hose, in the lumen of which a spacer is arranged, at least in sections, to reduce the lumen, more particularly the free lumen. Such a hose is preferably made of a flexible material, more particularly a flexible plastic, which, more particularly, is squeezable in sections.

In accordance with a further, particularly preferred form of embodiment of the invented hose segment, the lumen of the hose segment is irregularly reduced by the spacer, i.e. when squeezed the lumen cannot be completely closed by the internal walls of the hose, but at least in the immediate vicinity of the pacer a lumen area remains through which the fluid can flow.

The hose segment also has a clear inner diameter which is between 0.2 mm and 10 mm, preferably between 0.5 mm and 5 mm and more particularly around approx. 3 mm. In a further form of embodiment the spacer is an integral part of the hose segment and/or the space is formed by an elongated, more particularly thread-lie or rod-like element which at least in sections is connected positively, non-positively or bonded to the hose segment and reduces the lumen to a value of between 0.01% to 5%, preferably between 0.1% and 1%, and more particularly around 0.5% so that through this the lumen of the hose segment in the perfused setting is slightly open and a volumetric flow of between 0.1 ml/mm and 8 ml/mm, preferably between 0.5 ml/min and 5 ml/min can be provided. The spacer in accordance with the invention is preferably partially made of material selected from a group which preferably includes plastic, wool, cotton, cellulose, metal, combinations thereof and suchlike and preferably has a cross-sectional shape that is quadratic, rectangular, oval, circular, square or suchlike.

The invention will be described below with the aid of a preferred form of embodiment, wherein it is pointed out that the invention is not restricted to the illustrated embodiment but also covers appropriate deviations in the sense of the present invention.

DETAILED DESCRIPTION OF THE PRESENTLY PREFERRED EMBODIMENTS

FIG. 1 schematically shows the structure of a device for pressure measurement with water-filled disposable catheters. In addition to the bag with an infusion solution 1 and a pressure cuff 2, a pressure transducer 3 and two-way valves 4 before the pressure sensors are shown. Adjoining this are three-way valves 5 and the corresponding lines are designated as $P_{ura}$ 7, $P_{ves}$ 8 and $P_{abd}$ 9. Via the pressure transmission hoses 10 the infusion solution is taken from the bag 1 to the rectal catheter 11 and the UPP catheter 12. In addition from the bottle 16 with, for example, a saline solution, via the roller pump 14 and the drip chamber 13, the saline solution is supplied to the UPP catheter 12 from the bottle 16.

The preparation and measuring procedure is carried out as follows:
a) The pump hose 15 is inserted into the pump 14 and the spike connection 12 of the hose inserted into the bottle stopper. The pump 14 is switched on until the drip chamber 13 of the bottle 16 is half filled and the hose is filled with saline solution completely free of bubbles.

b) The three pressure measurement indicators 6 are placed in the holders and connected to the perfusion hose 18—between the perfusion hose and one pressure measurement indicator a flow transducer 3 is inserted. The spike connection 19 of the perfusion hose 18 is inserted into the water bags 1.
c) The pressure transmission hoses 10 are connected to the pressure measurement indicators 6.
d) All two-way 4 and three-way valves 5 are closed and the pressure cuff 2 is pumped up to pressurise the water bags 1.
e) To vent the pressure transmission tubes the two-way 4 and three-way valves 5 of the pressure transducer are set to "open" and are filled, without bubbles, to the top with water and the two-way valve 2 is closed again. This procedure must be carried out individually for all three pressure transmission lines.
f) The three-way valves 9 are now individually turned into the 90° position in order to electronically adjust the pressure channel to atmospheric pressure by pressing a button. The three-way valves 5 are then turned to the "open" position again.
g) The two catheters 11, 12 are placed in the urethra and rectum of the patient and connected to the pressure transmission lines and the pump hose 10.
h) The three-way valves 5 must now be individually opened again individually in order to vent the two lumens of the transurethral catheter 12 up to the tip and to fill the balloon of the rectal catheter 11.
i) The measured pressures are checked and, if necessary, zeroed by software. The system is now ready for measurement.

Figure 2:
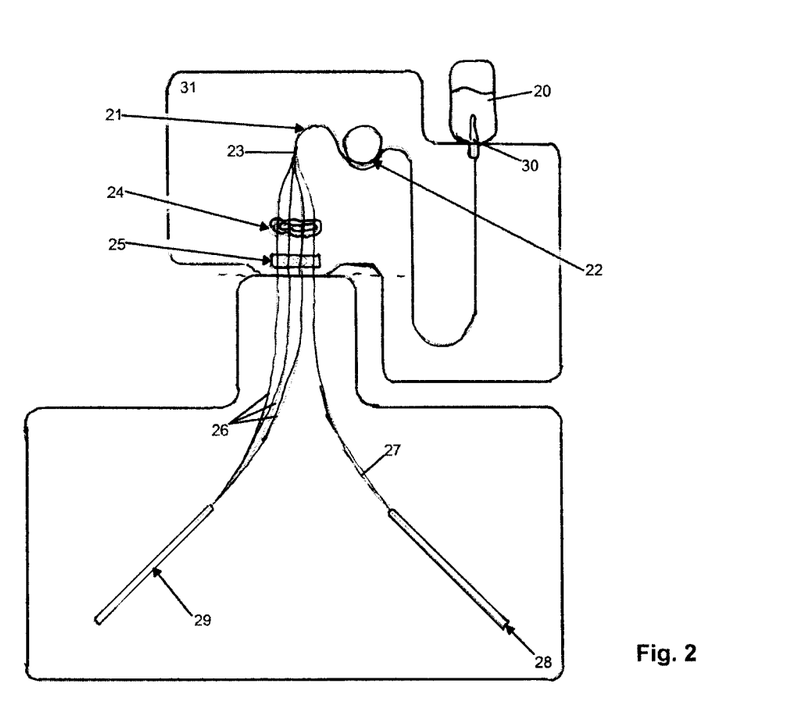
FIG. 2 shows the structure of a pressure measuring system with a device for regulating a volumetric flow in accordance with the invention.

In FIG. 2 the set-up of a pressure measuring system in accordance with the invention is shown.

With reference number 21 this figure shows the pump hose leading to the pressure dome cassette 25 with the Luer locks for the connection of catheters 28 and 29. The spike connector 30 for standard infusion bottles 20 is also shown. 29 denotes the transurethral and 28 the rectal catheter (possible also any number of catheters or measuring volumes) which are supplied with the fluid via the lines 26 (three stages) and 27. Arranged adjoining this is the locking mechanism of the dome cassette 25. Arranged in the area denoted as 24 are four (possibly any number) of hose clips with the statuses "open", "closed" and "perfused". A roller pump 22 for conveying the medium through the hose system is shown. The system also has a control system 21 with a fully automated algorithm for venting the hose system with catheters, determining rest pressure and zeroing the measuring system using the functionality of the individual components.

In FIGS. 3a-3h various positions (open, close, perfused) of the device 41 for regulating the volumetric flow, i.e. the hose clamp.

Figure 3A:
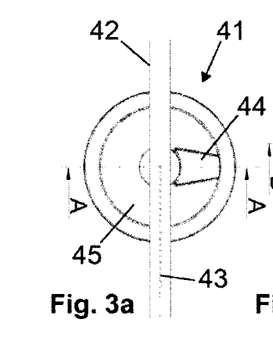
FIGS. 3a-3h show detailed views of the device for regulating the volumetric flow.

In the upper row 3a to 3c a view from above of a corresponding device 41 is shown, in which the hose 42 is inserted. In the hose in the lower half, a thread 43 in the form of a spacer can be seen. In addition, the clamping element 44 and, interacting with it, the counter-wall 45 of the device 41 is shown. In FIG. 3a the open position, in FIG. 3b the completely closed position and in FIG. 3 the so-called perfused, i.e. slight open, position is shown.

Figure 3B:
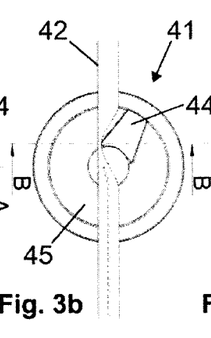
Figure 3C:
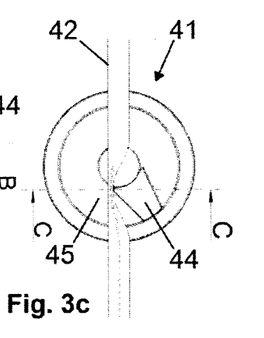
Figure 3D:
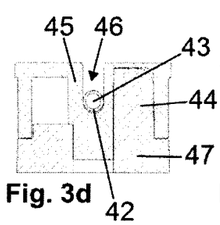
Figure 3E:
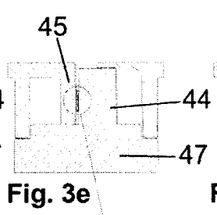
Figure 3F:
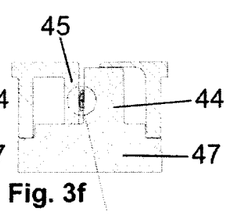
Figure 3G:
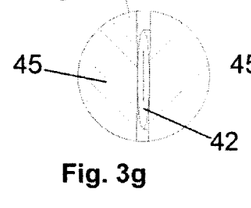
Figure 3H:
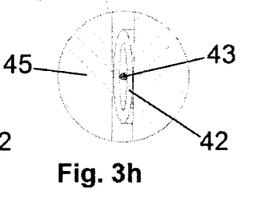

FIGS. 3d to 3f show cross-sectional views from FIGS. 3a to 3c along the relevant lines A-A, B-B and C-C. Here too the inserted hose 42 with the space 43 can be seen which is placed in the accommodating section 46 of the device. Reference number 44 denotes the clamping element which is arranged on a rotatable guide 47. The latter can interact with the wall section 45 in the various position (see 3c and 3f), wherein in accordance with the view shown here, in the position according to FIGS. 3b and 3e the hose is completely closed and in the position according to FIGS. 3c and 3f the hose is slightly open, although the clamping element 44 interacts with the counter-wall 45. However, in spite of squeezing of the hose, the spacer 43 brings about a slight fluid flow. In FIGS. 3g and 3h detailed views of the two positions 3e and 3h are shown in order to illustrate the difference between closed and perfused. The slight opening of the hose can be clearly seen in FIG. 3h.

Such a device 41 can also be called a hose clamp. The hose clamps replace the two-way and three-way valves used in conventional pressure measurement. They also act as a perfusion regulator for pressure measurement channels that have to be perfused (urethral pressure in urodynamic). The clamps can be brought into the positions "open", "closed" and "perfused" by simply turning about the axis with any actuator.

Position "open": in this position the filling medium can pass the hose clamp unhindered. It is the start and end position for all channels in which the hose system can be simply inserted or removed, is also used for venting the measuring channel and is the normal operating state of the infusion channel.

Position "closed": in this position the hose is completely clamped and even at pressure differences up to 2 bars it is impassable for the fluid. It is the operating state for already vented measuring channels and the temporary initial state for the infusion channel when the measuring channels are vented or perfused.

Position "perfused": in this position, largely independently of the admission pressure, only very small quantities of the filling medium (max. 8 ml/min) can pass the clamping point. This is achieved in that even though the hose is clamped with full force in similar manner to the "closed position", in the wall of the hose a small opining is always kept free by a spacer, such a thread, which brings about a capillary reduction of the filling medium flow. This position is used for channels which require perfusion (urethral pressure).

Figure 4:
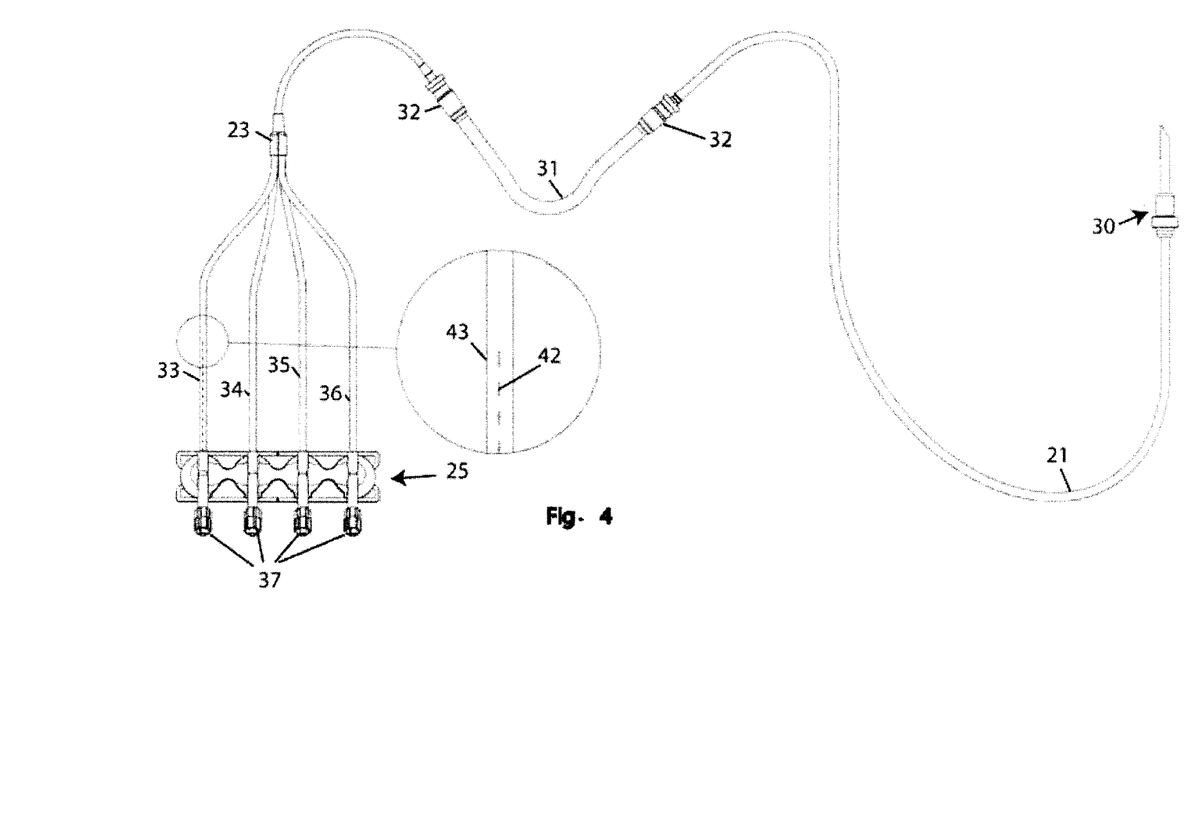
FIG. 4 shows a detailed view of a pump hose for the pressure measuring system in accordance with the invention.

Integrated in the pump hose—as shown in FIG. 4—are the infusion hose 21, the venting hoses 34 to 36 for the three—possibly any number of—pressure channels and the dome cassette 25. The pump/infusion hose 21 also has a spiked connection 30 for an infusion bag and Luer locks 37 for connection of the catheter. When using the system with a roller pump the hose system has a suitable compressible hose segment 1 in this segment which it integrated into the hose system through appropriate connectors. Via the distributor 23 the hose system is dispersed over the four hoses 33 to 36 shown here. In addition to the actual hose 42, the hose 33 also comprises the spacer 43 as can be seen in the detailed view in FIG. 4.

Particularly advantageous in the present invention is the integration of three—possibly any number of—domes in a dome cassette and the joint coupling of the channels to the sensors via a pressing roller and clamping edge. The webs integrated into the dome cassette act on the pressing roller and clamping edge side as spring elements, which produce the required pressing pressure of the membranes, which are preferably arranged on the base section of the pressure domes, on the sensors.

This design has the great advantage over the conventional solution with individual domes in that production is very much more cost-effective and handling is extremely simplified. Instead of placing each dome individually on its sensor as in the previous solutions, it is sufficient to insert the cassette which through the subsequent pressing of a button is turned with the pressing roller into the "closed" position via an actuator. The previously high number of required sterile components is reduced to a single disposable product.

As in many areas of application the sensors can be placed above the measuring locations in the body, as a result of the hydrostatic force of the water column negative pressures (lower than atmospheric pressure) also occur in the dome which are then not measured through pressure on the sensor surface but through tension. To produce the suction effect required for this the contacting between the membranes and sensor must be completely airtight. For this a pressing force is required.

Figure 5:
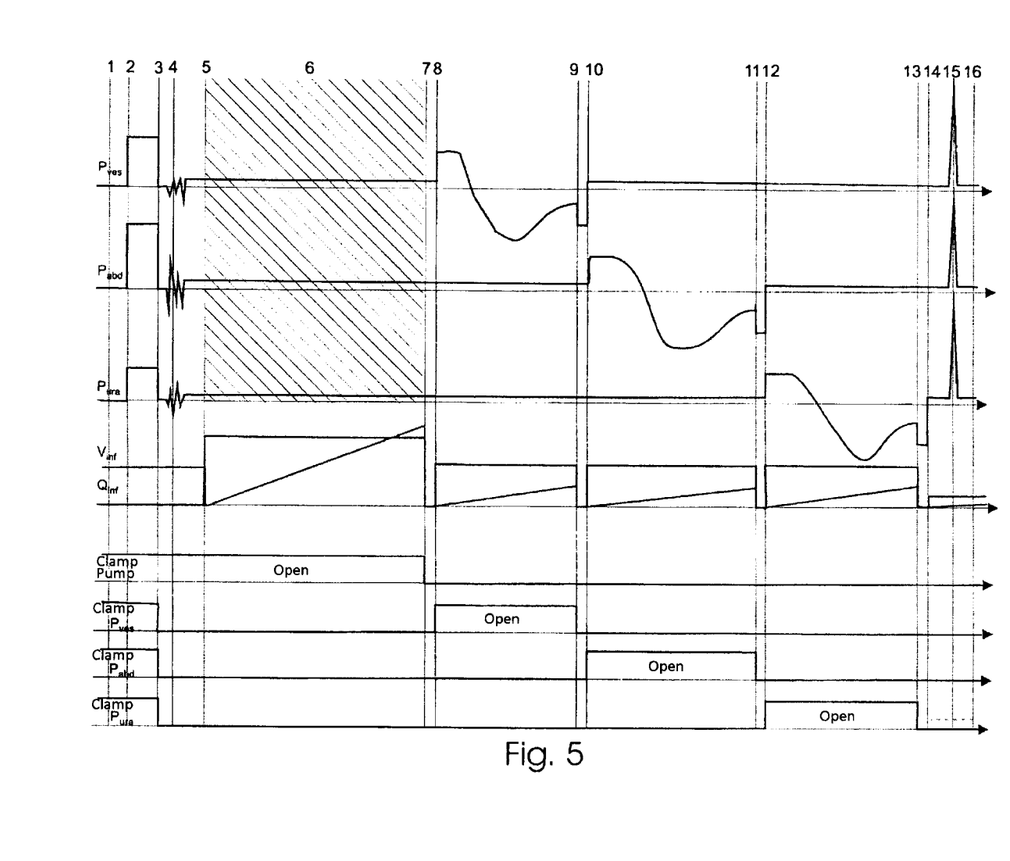
FIG. 5 shows the measuring report for automatic venting and zeroing of the pressure measuring system in accordance with the invention.

In FIG. 5 by way of the process stages the course of the pressure at the corresponding positions or settings of the components is shown. $P_{ura}$, $P_{ves}$, and $P_{abd}$ stand for the pressure in the corresponding pressure domes, $V_{inf}$ and $Qi_{nf}$ for the infusion volume and the fluid flow and clamp pump, clamp $P_{ura}$ clamp $P_{abd}$ and clamp $P_{ves}$ for the switching position of the corresponding tube clamp. The process is described as an example below:

1) The user places the dome cassette 25 of the pump hose 21 into the device and inserts the spike connection 30 into the infusion bag 20.
2) The locking mechanism is closed, whereby through the pressing pressure of the domes 25 on the sensors a pressure offset occurs.
3) The pressure offset is automatically balanced out (zeroed) after a material relaxation time of 5-10 seconds. At the same times the hose clamps 24 of the pressure channels 26 and 27 are closed.
4) The user places the transurethral catheter 29 in the bladder and the rectal catheter 28 in the rectum of the patient (if this has not already been done) and connects the pump hose 21 and the pressure transmission hoses with the Luer locks of the dome cassette. As of this moment the user can check the correct placement of the catheter 28, 29 by means of rest pressure values shown on the device, which are now measured via the air columns of the pressure transmission hoses and catheter lumen.
5) If the rest pressures show plausible values, the user starts the fully automatic venting and zeroing procedure by pressing a button on the device, whereupon the entire infusion line is vented.
6) In the hatched time interval all the measuring changes measure the rest pressure at the relevant measuring site via the air column. In order to minimise any fluctuations through movement of the patients or disturbances the average value measured by the channel during this period is calculated and is subsequently used as the rest pressure value for zeroing.
7) As the volume of the infusion line (tube plus filling volume of the catheter) is precisely known and the quantity of the filling medium conveyed through the volume transducer and rotations of the rolling wheel of the pump 22 is constantly measured, the venting can be fully automatically ended when the water column reaches the filling lumen output. The pump hose clamp 24 is closed.
8, 10, 12) The venting of the pressure transmission hoses then always takes sequentially in the same way. The relevant hose clamp is opened, while all the others are closed and the pump conveys the filling medium at a defined filling rate through the relevant pressure transmission line. It should be noted, that during filling, due to the increasing water column a hydrostatic and also a dynamic component are increasingly added and no longer is the actual pressure at the measuring location determined.

9, 11, 13) As the volumes of the pressure transmission lines are known and the filling quantity is constantly measured the venting process can be fully automatically ended when the water column has reached the measuring lumen outputs. The pump 22 is stopped and the relevant hose clamp closed. At this moment the device measures the current pressure at the measuring location in the body plus a hydrostatic pressure resulting from the unknown difference in height between the measuring location and the sensor. This is now fully automatically calculated by setting the measuring channel to the rest pressure measured via the air column in (6) by means of the software.

14, 15) The correct placement of the catheter is checked in a final stage by asking the patient to cough and comparing the resulting pressures peaks. For this the hose clamps 24 of all channels which require perfusion for the measurement ($P_{ura}$ in urodynamics) are automatically set to the perfusion setting and the pump 22 to perfusion speed.

16) The preparatory phase is completed and the actual measurement can begin.

The invention claimed is:

1. A device for regulating a volumetric flow of a fluid, the device comprising:
    a hose segment having a lumen through which the fluid can flow and having a closable region and a perfusion region;
    a hose clamp including a housing with an accommodating region for the hose segment and a clamping element adapted to move rotationally about a center of rotation in a first direction and in a second direction that is opposite to the first direction among a closed regulation position, an open regulation position and a perfused regulation position, and in interaction with first and second sections of the accommodating region as first and second pressing points on the closable region and the perfusion region, respectively, of the hose segment, at least one counter-pressure element of the clamping element acting on the hose segment to achieve the closed regulation position and the perfused regulation position, respectively;
    for the perfused regulation position a spacer is arranged in the lumen of the hose segment at least in the perfusion region; and
    the device can be set, without movement of the center of rotation along the lumen of the hose segment, to at least the closed regulation position, the open regulation position and the perfused regulation position when the clamping element is moved rotationally about the center of rotation, wherein (i) in the closed regulation position the lumen of the hose segment is completely closed in the closable region when the clamping element is rotated in the first direction, (ii) in the perfused regulation position the lumen of the hose segment is kept at least partially open by the spacer in the perfused region of the hose segment when the clamping element is rotated in the second direction, and (iii) the open regulation position is achieved by rotating the clamping element between the closed and perfused regulation positions.

2. The device according to claim 1 wherein in the perfused regulation position the lumen of the hose segment is kept slightly open by the spacer in the perfused region of the hose segment.

3. The device according to claim 1 wherein the first and second pressing points are formed by first and second counter-pressure elements, respectively, of the clamping element.

4. The device according to claim 1 wherein the clamping element is moved about the center of rotation by a motor among the closed regulation position, the open regulation position and the perfused regulation position and is held by the motor in each of the closed regulation position, the open regulation position and the perfused regulation position, respectively.

5. The device according to claim 1 wherein the device, the hose clamp, the hose segment or parts thereof are at least in sections made of a material that is selected from a group that includes duroplastic or thermoplastic synthetic materials.

6. The device according to claim 1 wherein the fluid is selected from a group which includes water, aqueous solutions, solutions for injection, solutions for infusion, nutritional solutions, electrolyte solutions, blood, plasma, gas, air, and combinations thereof.

7. The device according to claim 1 wherein the hose segment is made of a flexible material and is squeezable in sections.

8. The device according to claim 1 wherein the lumen of the hose segment has an inner diameter of between 0.2 mm and 10 mm.

9. The device according to claim 1 wherein at least one of (i) the spacer is an integral component of the hose segment and in the perfusion region reduces the lumen of the hose segment and (ii) the spacer is formed by an elongated element that reduces the lumen of the hose segment and that at least in sections is connected to the hose segment in the perfusion region.

10. The device according to claim 1 wherein the reduction in the lumen by the spacer is between 0.01% to 5%, through this the lumen of the hose segment in the perfused regulation position is kept slightly open so that a volumetric flow of between 0.1 ml/mm and 8 ml/mm is provided.

11. A device for regulating a volumetric flow of a fluid, the device comprising:
a hose segment having a lumen through which the fluid can flow and having a closable region and a perfusion region;
a hose clamp including a housing with an accommodating region for the hose segment and a clamping element adapted to move rotationally about a center of rotation in a first direction and in a second direction that is opposite to the first direction among a closed regulation position, an open regulation position and a perfused regulation position;
the clamping element defining two counter-pressure elements, wherein (a) one of the counter-pressure elements acts on the closable region of the hose segment to achieve the closed regulation position and (b) another of the counter-pressure elements acts on the perfusion region of the hose segment to achieve the perfused regulation position;
for the perfused regulation position a spacer is arranged in the lumen of the hose segment at least in the perfusion region; and
the device can be set, without movement of the center of rotation along the lumen of the hose segment, to at least the closed regulation position, the open regulation position and the perfused regulation position when the clamping element is moved rotationally about the center of rotation, wherein (i) in the closed regulation position the lumen of the hose segment is completely closed in the closable region when the clamping element is rotated in the first direction to press one of the counter-pressure elements against the closable region, (ii) in the perfused regulation position the lumen of the hose segment is kept at least partially open by the spacer in the perfused region of the hose segment when the clamping element is rotated in the second direction to press the other of the counter-pressure elements against the perfused region, and (iii) the open regulation position is achieved by rotating the clamping element between the closed and perfused regulation positions.

12. The device according to claim 11 wherein, when the device is set in the perfused regulation position, the lumen of the hose segment has capillary flow by the spacer in the perfused region of the hose segment.

13. The device according to claim 11 wherein the clamping element is moved about the center of rotation by a motor among the closed regulation position, the open regulation position and the perfused regulation position and is held by the motor in each of the closed regulation position, the open regulation position and the perfused regulation position, respectively.

14. The device according to claim 11 wherein the hose segment is made of a flexible material and is squeezable in sections.

15. The device according to claim 11 wherein the hose segment has a clear inner diameter of between 0.2 mm and 10 mm.

16. The device according to claim 11 wherein at least one of (i) the spacer is a spacer element that is an integral component of the hose segment and (ii) the spacer is a spacer element that is formed by an elongated element that is connected to the hose segment.

17. The device according to claim 11 wherein the lumen of the hose segment in the perfused setting is kept slightly open so that a volumetric flow of between 0.1 ml/mm and 8 ml/min is provided.

18. The device according to claim 16 wherein the spacer element is at least partially made of a material selected from a group that includes plastic, wool, cotton, cellulose, and metal.

19. The device according to claim 11 wherein the spacer has a cross-sectional shape that is quadratic, rectangular, oval, circular, or square.

* * * * *